United States Patent [19]

Zuk et al.

[11] 4,256,834
[45] Mar. 17, 1981

[54] FLUORESCENT SCAVENGER PARTICLE IMMUNOASSAY

[75] Inventors: Robert F. Zuk, Mountain View; Edwin F. Ullman, Atherton, both of Calif.

[73] Assignee: Syva Company, Palo Alto, Calif.

[21] Appl. No.: 28,640

[22] Filed: Apr. 9, 1979

[51] Int. Cl.[3] .................. C12Q 1/66; A61K 37/00; G01N 31/00; G01N 23/00
[52] U.S. Cl. .................................. 435/7; 23/230 B; 424/8; 424/12; 435/5; 435/810
[58] Field of Search ............. 435/7, 810; 424/1, 1.5, 424/8, 12; 23/230 B

[56] References Cited

U.S. PATENT DOCUMENTS

| | | | |
|---|---|---|---|
| 3,720,760 | 3/1973 | Bennich et al. | 424/8 |
| 4,108,972 | 8/1978 | Dreyer | 424/8 |
| 4,115,535 | 9/1978 | Giaever | 424/12 |
| 4,130,462 | 12/1978 | Rubenstein et al. | 424/12 |
| 4,134,792 | 1/1979 | Boguslaski et al. | 435/7 |
| 4,160,645 | 7/1979 | Ullman | 424/12 |
| 4,161,515 | 7/1979 | Ullman | 23/230 B |
| 4,166,104 | 8/1979 | Wagner et al. | 424/1 |
| 4,193,983 | 3/1980 | Ullman et al. | 23/230 B |

*Primary Examiner*—Thomas G. Wiseman
*Attorney, Agent, or Firm*—Bertram I. Rowland

[57] ABSTRACT

Novel immunoassays are provided employing discrete particulate reagents for determining an analyte which is a member of a specific binding pair-ligand and homologous receptor. The assay employs as a first reagent, a member of said pair bound to an insoluble particle (particle conjugate); as a second reagent, a label which is part of a signal producing system, bound to a member of said pair (signal label conjugate); and as a third reagent, a signal repressor comprising an insoluble particle, where the signal repressor is obstructed from interacting with said label of said signal label conjugate, when said signal label conjugate is bound to said particle conjugate.

In performing the assay, the analyte, the reagents, and any ancillary materials are combined in an aqueous assay medium and the signal determined as compared to an assay medium having a known amount of analyte.

The repressor greatly enhances the sensitivity and accuracy of the immunoassay in repressing the signal produced by labels which are not bound to the particle conjugate, thus substantially limiting the observed signal to label bound to the particle conjugate. The labels which are employed provide a signal which does not differ significantly from when the signal label conjugate is bound to the particle conjugate or is free in the bulk solution. Illustrative labels include chromogens, such as fluorescers, chemiluminescers, and the like.

Particular reagents and kits are provided, where the kits have predetermined amounts of the various reagents to substantially optimize the sensitivity of the assay.

23 Claims, No Drawings

FLUORESCENT SCAVENGER PARTICLE IMMUNOASSAY

BACKGROUND OF THE INVENTION

1. Field of the Invention

The interest in analyzing for trace amounts of a wide variety of organic materials, such as drugs, contaminants, pollutants, and the like, has engendered efforts to provide simpler and more accurate techniques for measuring low concentrations of compounds of interest. One group of techniques is referred to as immunoassays, which are based on the ability to have a compound, usually an antibody, which is capable of recognizing or specifically binding to a compound having a specific spatial and polar organization. The specific binding pair may be referred to as ligand and receptor (antiligand).

In performing the immunoassays, normally the ligand is labeled with a label which provides a detectible signal and the labeled ligand is allowed to compete with the ligand in the sample for a limited amount of the antiligand. The immunoassay techniques then provide for distinguishing between the associated labeled ligand and antiligand and dissociated labeled ligand which is free in the bulk solution. Distinguishing the associated signal label may be achieved by separating the unassociated signal label from the associated signal label and determining the amount of signal label in either of the fractions.

A preferred method is to employ a procedure which does not require separation; one distinguishes associated signal label from unassociated signal label by there being a substantial difference in the level of signal between the two. One of the problems with the latter technique is the fact that the signal label which is measured is not freed from materials present in the assay system which may provide a background or cause non-specific interference with the signal measurement.

For many ligands of interest, particularly large molecules, such as proteins, polysaccharides, nucleic acids, and the like, obtaining the ligand in pure form is frequently difficult, and in some instances impossible. Furthermore, where the antiligand is an antibody, the antibody is normally isolated as a complex mixture of globulins, of which a portion, usually less than 50%, is the antibody of interest. Where one is labeling the impure ligand or antiligand, a substantial proportion of the label will be conjugated to molecules other than the ligand or antiligand. These labels will be capable of providing a detectible signal, which will act as a background for the measurement. That is, these labels will provide a base value which will be additive to the value obtained from the label bound to the ligand or antiligand. Where one is determining a small value between two large values, substantial errors and uncertainities are introduced. For example, where there are non-specific effects affecting the label, the presence of a large amount of label unrelated to ligand or antiligand will greatly increase the variability due to the non-specific effects on a sample-by-sample basis.

It is therefore desirable to provide techniques which will allow for discrimination between label bound to ligand or antiligand participating in the assay and related to the amount of analyte in the assay and label which is present which is not involved with ligand or antiligand. The techniques provided must, therefore, be able to discriminate between the label which is providing signal related to the amount of analyte in the medium and the signal being obtained from label unrelated to the amount of analyte in the medium.

2. Description of the Prior Art

Engasser and Horvath, Applied Biochem. Bioengineering, Vol. I, 127 (1976) Academic Press, report the kinetic and diffusion effects on the immobilization of enzymes. U.S. Pat. No. 3,817,837 describes a homogeneous enzyme immunoassay. U.S. Pat. No. 3,996,345 describes a homogeneous immunoassay employing two chromophores related by being a fluorescer and a quencher. Copending application Ser. No. 815,636, U.S. Pat. No. 4,160,645 filed July 14, 1977, describes a homogeneous immunoassay employing a nonenzymatic catalyst as a label, while copending application Ser. No. 815,632, U.S. Pat. No. 4,208,479, describes means for modulating signals in immunoassays. Copending application Ser. No. 906,514, U.S. Pat. No. 4,193,983, filed May 16, 1978, describes a labeled liquid discontinuous phase for use in immunoassays. Application Ser. No. 667,996, abandoned, filed Mar. 18, 1976, describes a homogeneous immunoassay employing as a label an enzyme substrate. See also U.S. Pat. No. 3,853,987, which discloses particles to which are conjugated radioactive and fluorescent labels and antibodies. See also U.S. Pat. No. 4,001,400. See also copending application Ser. No. 964,099, filed Nov. 24, 1978.

SUMMARY OF THE INVENTION

The subject invention provides methods and compositions for determining the presence of an organic analyte, which is a member of a specific binding pair, i.e. ligand and its homologous receptor (antiligand). The method is predicated upon the ability to partition a chromogenic substance between a phase where the chromogenic substance retains its chromogenic activity and a phase where its chromogenic activity is repressed, with the degree of partitioning being a function of the concentration of analyte in the assay medium.

The method employs three reagents: (1) a conjugate of a member of the specific binding pair with an insoluble particle (particle conjugate); (2) a label which is a member of a signal producing system conjugated to a member of said specific binding pair (signal label conjugate); and (3) a signal repressor which is an insoluble particle which interacts with said label to repress the contribution of the label to signal production.

In carrying out the assay, the unknown suspected of containing the analyte, the above three reagents, and any ancillary reagents are combined in an assay medium in accordance with a predetermined protocol and the signal level determined from the assay medium, either by a rate or equilibrium mode. When the signal label conjugate binds to the homologous member of the particle conjugate, the signal repressor is obstructed from interacting with the label associated with the particle conjugate. Signal label conjugate in the bulk solution interacts with the signal repressor, resulting in inhibition of signal production from such signal label. The number of signal label conjugates able to bind to the particle conjugate will be a function of the number of analyte molecules in the assay medium. Thus, the observed signal level will be a function of the number of analyte molecules in the assay medium. By comparing the observed signal level with an unknown amount of analyte with the signal level obtained with at least one assay medium having a known analyte concentration, the analyte concentration of the unknown can be qualitatively or quantitatively determined.

Reagent compositions and kits are provided, where the kits have predetermined amounts of compositions and ancillary materials to substantially optimize the sensitivity and reliability of the assay.

DESCRIPTION OF THE SPECIFIC EMBODIMENTS

A sensitive, accurate simple assay method is provided for determining low concentrations of a wide variety of organic materials. The materials of interest include those having physiological activity, drugs or naturally occurring compounds present in physiological fluids, disease related materials, contaminants, pollutants, and the like.

The method does not employ a separation step, maintaining a substantially uniform dispersion and also minimizes background interference. The method affords a reduction in signal from materials or labels which are unrelated to the signal label bound, directly or indirectly, with ligand receptor in the medium. Also, the subject method provides substantial advantages with analytes which normally exist in impure form and are not readily amenable to purification.

In preparing reagents for immunoassays, it is normally required to label either the ligand or its homologous receptor. The homologous receptor, particularly when antibody, is normally a mixture of specific and non-specific immunoglobulins. With many antigens, the low concentrations of the antigens make their purification or concentration tedious, inefficient and expensive. Therefore, frequently, when labeling a member of the specific binding pair, one labels the impure mixture.

Labeling of the impure mixture creates a number of problems. One problem is that there will be a substantial amount of adventitious label unrelated to the assay reagents. The second problem is the measurement of the signal label associated with the ligand or antiligand in the presence of a large amount of adventitious label. A third problem is non-specific interactions of the adventitious signal label which can cause sample-to-sample variation unrelated to the amount of analyte.

The subject method alleviates or cures these problems by a unique combination of reagents. The first reagent has a member of the specific binding pair bound to a particle. By employing high molecular weight particles, one can insure that one can bond the specific bonding pair member as well as impurities to the particles, with each particle conjugate being an active reagent in the assay.

The second reagent is a signal label conjugate, where a member of the specific binding pair is labeled with a member of a signal producing system. The member of the specific binding pair may be pure or impure. In the assay, the amount of the labeled member of the specific binding pair which binds to the particle conjugate will be related to the amount of analyte in the medium. Only labels which are bound to a member of the specific binding pair can become bound to the particle conjugate.

As a third reagent, included in the assay medium, is a signal repressor which interacts with the signal label to significantly inhibit the production of a signal by the label. The signal repressor is an insoluble particle which is obstructed from interacting with label which is bound to the particle conjugate. Therefore, only label which is free in the bulk solution will be significantly inhibited by the signal repressor. Signal labels which, are unbound, adventitiously bound to compounds other than members of the specific binding pair, or bound to a member of the specific binding pair which is not bound to the particle conjugate, will interact with the signal repressor and their contribution to production of a signal substantially inhibited. In this manner, relatively impure mixtures of a member of the specific binding pair may be labeled without concern about introducing a large background signal level, since the signals from these labels will be substantially repressed by the signal repressor.

Both the particle conjugate and the signal repressor will be discrete, insoluble particles. The nature of the particles is chosen, so that the signal repressor is obstructed from interacting with signal label which is bound to the particle conjugate through noncovalent binding with the reciprocal member of the specific binding pair.

The analyte will be a member of a specific binding pair, consisting of ligand and its homologous receptor. The insoluble particles employed for the particle conjugate will be bound, directly or indirectly, covalently or noncovalently, to one of the members of the specific binding pair. There is an exception where a receptor is the analyte. Because of the dual nature of the receptor, two specific binding pair couples may be employed. For example, a ligand recognized by the receptor analyte may be conjugated to the particle to form particle conjugate. Receptor for the receptor analyte (antireceptor) may be conjugated to a label to form the signal label conjugate. In this way, one has the alternative to use either a single specific binding pair or two specific binding pairs, employing the duality of properties of the receptor.

In carrying out the subject method, one combines in an appropriate assay medium, the analyte containing sample, the particle conjugate, the signal label conjugate and the signal repressor, as well as any additional reagents and determines the signal from the assay medium. By comparing the observed signal with the signal obtained from an assay medium having a known amount of analyte, one can qualitatively, semi-quantitatively, or quantitatively determine the analyte of interest. The significant factor in the subject assay, is that one employs two particulate species, which by virtue of their physical structure sterically inhibit interaction between a molecule on one particle and the second particle or molecule bound to the second particle. The second particle is able to interact with label unassociated with the first particle and free in the bulk solution to substantially inhibit the production of a signal by such signal labels.

DEFINITIONS

Analyte—the compound or composition to be measured, which may be a ligand, which is mono or polyepitopic, antigenic or haptenic, a single or plurality of compounds which share at least one common epitopic site or a receptor.

Specific binding pair—two different molecules, where one of the molecules has an area on the surface or in a cavity which specifically binds to a particular spatial and polar organization of the other molecule. The members of the specific binding pair are referred to as ligand and receptor (antiligand).

Ligand—any organic compound for which a receptor naturally exists or can be prepared.

Receptor (antiligand)—any compound or composition capable of recognizing a particular spatial and polar organization of a molecule i.e. determinant or epitopic site. Illustrative receptors include naturally occurring receptors, e.g. thyroxine binding globulin, antibodies, enzymes, Fab fragments, lectins and the like.

Ligand Analog—a modified ligand which can compete with the analogous ligand for a receptor, the modification providing means to join a ligand analog to another molecule. The ligand analog will normally differ from the ligand by more than replacement of a hydrogen with a bond which links the ligand analog to a hub or label.

Poly(ligand analog)—a plurality of ligands or ligand analogs joined together covalently, normally to a hub nucleus. The hub nucleus is a polyfunctional material, normally polymeric, usually having a plurality of functional groups e.g. hydroxy, amino, mercapto, ethylenic, etc. as sites for linking. The hub nucleus may be water soluble or insoluble, preferably water soluble, and will normally be at least about 35,000 molecular weight and may be 10 million or more molecular weight, but usually under 600,000, more usually under 300,000. Illustrative hub nucleii include polysaccharides, polypeptides, including proteins, nucleic acids, ion exchange resins and the like. Water insoluble hub nucleii may be the same as those indicated for the particle.

Particle (insoluble phase)—the particle conjugated with a member of the specific binding pair is a discrete particle, which may be swelled or remain unswelled by the liquid phase, may be solid or liquid, and composed of a wide variety of both hydrophobic and hydrophilic materials. Depending upon the role of the particle, the particles may be solid, hollow or porous, having a substantially smooth or irregular surface, having a primarily concave or convex surface, for some applications, preferably being porous, that is, having channels, fractures or indentations, which can be widely varied as to the size of molecule or assembly which is excluded or whose rate of diffusion is substantially affected. For other applications, the particle will desirably be solid, having a smooth or irregular surface. The particles may be stable discrete liquid particles, such as dispersed surfactant stabilized oil particles, liposomes, or the like. The particles will be readily dispersible in an aqueous medium, and for the particle conjugate and in some instances the signal repressor be polyfunctionalized or capable of polyfunctionalization for binding, covalently or non-covalently, to other molecules. The particles of the particle conjugate will be preferably substantially transparent to light at wavelengths used for detection of a signal produced by the signal producing system, particularly in the range between 300 and 800 nm, preferably through the range.

Signal producing system—the reactants and products involved in producing a measureable signal, which varies with the amount of analyte in the assay medium. The signal producing system may have one or more components, at least one component being conjugated to a specific binding pair member not covalently bonded to a particle. The signal producing system produces a measurable signal which is detectible by external means, the measurement of electromagnetic radiation, with the level of signal varying to the extent the signal label conjugate is in the environment of the solid phase particles. The signal producing system will contain a chromophore, where chromophores include dyes which absorb light in the ultraviolet or visible region, phosphors, fluorescers, chemiluminescers, light emitting energy acceptors, chromogenic enzyme substrates and the like. With fluorescers, the fluorescer may be excited by light or by an energy donor molecule, while with chemiluminescers, the excitation will be the result of a chemical reaction.

Label—the label is a molecule which has a particular function and is conjugated to another molecule or material. In the subject invention, the labels will be the specific binding pair molecule that is conjugated to the particle (particle conjugate) or a molecule which is part of the signal producing system that is conjugated to a member of the specific binding pair or to a particle.

Particle conjugate—the particle to which is bound, directly or indirectly, a member of the specific binding pair, and, as appropriate one or more members of the signal producing system. Signal labels bound to the particle through the specific binding pair will be influenced by and in sufficient proximity to the particle surface, so that a signal repressor particle which would otherwise be able to interact with the label will be obstructed from interacting with the label. Thus, the signal repressor will be prevented from interacting with the signal label bound to the particle and affecting the signal emanating from the signal label. The particle conjugate will preferably be relatively nonadsorptive to minimize non-specific binding of proteins.

Binding pair label—a member of the specific binding pair bound, directly or indirectly, to the particle.

Signal label—a member of the signal producing system bound to a binding pair member or to the particle.

Signal label conjugate—the conjugate of the binding pair member with a member of the signal producing system (signal label).

Labeled ligand—the conjugate of the ligand member of the specific binding pair with a member of the signal producing system, either covalently or noncovalently bound, when covalently joined, either joined by a bond, linking group, or hub nucleus. The labeled ligand may have one or more ligands (includes ligand analogs) or one or more labels or a plurality of both, the latter being referred to as poly(ligand analog)polylabel.

Labeled receptor—the conjugate of receptor with a member of the signal producing system, where the two are bound either covalently or non-covalently, usually covalently by a linking group, there being one or more labels bound to the receptor or one or more receptors bound to a label.

Signal Repressor—a water insoluble, optionally swellable, particle, which may be solid, hollow or porous, may have a smooth or irregular surface, generally of indeterminate molecular weight, may be crosslinked or noncrosslinked, frequently crosslinked, may be naturally occurring or synthetic, absorptive in the wavelength range of interest, subject or not subject to non-specific protein binding, polyfunctionalized or nonfunctionalized for linking, and conjugated or unconjugated to specific compounds which interact with the signal label to diminish the signal produced by such label. The particle may or may not have an affinity or adsorptive capacity for signal label bound to a binding pair member and signal label bound to non-specific impurities, where present, but when having no affinity for signal label, it will be conjugated to a compound having affinity for signal label or signal label conjugate. The signal repressor may express its effect by virtue of the inherent properties of the particle or by virtue of particular functionalities or compounds conjugated to the particle. The signal repressor acts to inhibit the emission of light produced by signal label that is in juxtaposition or bound to the signal repressor.

METHOD

The subject assay is carried out in an aqueous zone at a moderate pH, generally close to optimum assay sensitivity, without separation of the assay components or products. The assay zone for the determination of analyte is prepared by employing an appropriate aqueous medium, normally buffered, the unknown sample, which may have been subject to prior treatment, the particle conjugate, the signal label conjugate, the signal repressor, all of the materials required for the signal producing system for producing a detectible signal, as well as members of the specific binding pair or their analogs, as required.

The presence of analyte—ligand or its homologous receptor (antiligand)—in the unknown sample will affect the partition of the signal label conjugate between the separate phase of the particle conjugate, where the signal label is protected from the signal repressor, and the bulk solution of the assay medium, where the signal label is subject to the signal repressor. Therefore, the observed signal will be related to the amount of analyte in the sample.

In carrying out the assay, an aqueous medium will normally be employed. Other polar solvents may also be included, usually oxygenated organic solvents of from 1 to 6, more usually from 1 to 4 carbon atoms, including alcohols, ethers and the like. Usually these cosolvents will be present in less than about 40 weight percent, more usually in less than about 20 weight percent.

The pH for the medium will usually be in the range of about 4–11, more usually in the range of about 5–10, and preferably in the range of about 6.5–9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the assay and usually constant temperatures during the period of the measurement, particularly for rate determinations. The temperatures for the determination will generally range from about 10°–50° C., more usualy from about 15°–40° C.

The concentration of analyte which may be assayed will generally vary from about $10^{-4}$ to $10^{-15}$ M, more usually from about $10^{-6}$ to $10^{-13}$ M. Considerations such as whether the assay is qualitative, semi-quantitative or quantitative, the particular detection technique and the concentration of the analyte of interest will normally determine the concentration of the other reagents.

While the concentrations of the various reagents in the assay medium will generally be determined by the concentration range of interest of the analyte, the final concentration of each of the reagents will normally be determined empirically to optimize the sensitivity of the assay over the range of interest. The total binding sites of the members of the specific binding pair which are reciprocal to the analyte will be not less than about 0.1 times the minimum concentration of interest based on analyte binding sites and usually not more than about 1,000 times the maximum concentration of interest based on analyte binding sites, usually about 0.1 to 100 times, more usually about 0.3–10 times the maximum concentration of interest. By concentration is intended the available concentration, that is, the concentration at saturation, and not necessarily the actual concentration where members of the specific binding pair may not be equally available for binding.

Depending upon the particular signal producing system, as well as the manner in which the specific binding pair members are employed, the amount of the various conjugates can be varied quite widely. For example, one could have very large excesses of the binding pair label in the particle conjugate, by first allowing the signal label conjugate containing the same binding pair member to react with the unknown, followed by combining with the particle conjugate. Where a competition mode is employed, in that the particle conjugate and the signal label conjugate contain the reciprocal binding pair members, large excesses of the binding pair label might reduce the sensitivity of the assay. By employing various concentrations of the various reagents with analyte at concentrations in the range of interest with a particular protocol, one can determine ratios which optimize the assay response.

The order of addition of the various reagents may vary widely, depending upon the particular labels, the compound to which the label is conjugated, the nature of the conjugates, the nature of the analyte, and the relative concentrations of the analyte and reagents. Also affecting the order of addition is whether an equilibrium mode or rate mode is employed in the determination. With fluorescers, normally an equilibrium mode is employed.

Since with many receptors, the association of the specific binding pair members is almost irreversible during the time period of the assay, one will normally avoid combining the particle conjugate with the signal label conjugate, prior to the addition of the analyte, where the two conjugates are reciprocal members of the specific binding pair. By contrast, where the two conjugates have the same member of the specific binding pair, one could combine them prior to introduction of the unknown sample into the assay medium.

A primary consideration of the subject assay is the role of the signal repressor in inhibiting the production of a detectible signal from signal label which is not bound to the particle conjugate. All protocols must take this role into account. Readings of the detectible signal will not be meaningful until the signal repressor is substantially at equilibrium in relation to the signal label in the bulk solution. Furthermore, a competition between the particle conjugate and signal repressor is undesirable. In the light of these considerations, protocols will normally allow for substantially complete equilibration between the particle conjugate, analyte and signal label conjugate, followed by the addition of the signal repressor. The first reading would then be taken after the signal repressor has had sufficient time to interact with the signal label in the bulk solution.

Where an enzyme is involved as part of the signal producing system a rate mode could be employed. Rate modes have the advantage of subtracting out inherent interferences, such as light scattering, signal production from substances unrelated to the label, equipment variations and the like.

One or more incubation steps may be involved in preparing the assay medium. For example, it may be desirable to incubate an antigen analyte with labeled receptor. In addition, it will frequently be desirable to have a second incubation after addition of the particle conjugate and a third incubation after addition of the signal repressor. Whether to employ an incubation period and the length of the incubation period, will depend to a substantial degree on the rate of binding of the receptor to the ligand and the signal label to the signal repressor. Usually, incubation steps will vary from about 0.5 min to 6 hrs, more usually from about 5 min to 1 hr. Incubation temperatures will generally range from about 4° to 50° C., more usually from about 15° to 37° C.

After the reagents are combined, the signal will then be determined. The method of determination is the observation of electromagnetic radiation, particularly ultraviolet and visible light, either absorption or emission. The signal will usually be read as electromagnetic radiation in the ultraviolet or visible region, particularly from about 250 to 750 nm, usually from about 350 to 650 nm.

The temperature at which the signal is observed will generally range from about 10° to 50° C., more usually from about 15° to 40° C.

Standard assay media can be prepared which have known amounts of the analyte. The observed signal for the standard assay media may then be plotted, so as to relate concentration to signal. Once a standard curve has been established, a signal may be directly related to the concentration of the analyte.

The time for measuring the signal will vary depending on whether a rate or single point measurement is used, the sensitivity required, the nature of the signal producing system and the like. For a rate mode, the times between readings will generally vary from about 5 sec to 6 hrs, usually about 10 sec to 1 hr, with the time for an individual reading generally being from about 0.1 sec to about 1 min.

The ligand may be mono- or polyepitopic. In most situations this difference will not affect the manner in which the assay is performed. Where the analyte is a ligand, the specific binding pair member in the particle conjugate may be either ligand or receptor. The signal label conjugate can have either ligand or receptor. However, where both the particle conjugate and the signal label conjugate have receptor, the ligand must be polyepitopic or made so by employing a poly(ligand analog) (includes poly(ligand analog)-label or -polylabel) as an additional reagent. That is, a sandwich technique is employed where the ligand binds to the particle conjugate and provides epitopic sites for binding of the signal label conjugate to the particle conjugate.

Where the receptor is the analyte, the particle conjugate and the signal label conjugate may have the same or different members of the specific binding pair, with the proviso that receptor is polyvalent when ligand is involved in both conjugates. Also, as indicated previously, the dual nature of the receptor may be utilized by having ligand bound to the particle as the particle conjugate and signal label bound to antireceptor as the signal label conjugate.

In the event that the analyte and the two conjugates all have or contain the same member of the specific binding pair, then the homologous member must be added and it must be provided in polyepitopic form, either as an antibody, or a polyvalent receptor, where it is a receptor or as polyhapten (poly(ligand analog)), where it is a ligand.

The subject assays provide great versatility in the manner in which the signal is produced and in the preparation of the reagents. The salient feature of the signal producing system is that the system produces a detectible signal, which is subject to repression, which repression can be obstructed when the signal producing label is bound to a particle through a specific binding pair. The manner of repression is physical, that is, the signal is repressed by changing the environment about the signal label. Therefore, a wide variety of combinations can be used for the signal label and the signal repressor.

In choosing the particle conjugate and the signal repressor, the two particles must be chosen to allow for the signal repressor to discriminate between signal label which is bound through a specific binding pair to the particle conjugate and signal label which is free in the bulk solution, present either as signal label conjugate or bonded to impurities. Conveniently, one could employ two differently derivatized or conjugated particles, which are both porous and a substantial proportion of the materials which are conjugated are within channels, pores or indentations of the particles. Therefore, any interaction between the signal repressor and the label associated with the particle conjugate would be solely limited to those groups on the surface of the particles, providing protection for labels within the particle's pores. The signal repressor particle, where porous, will be required to have channels or pores of a sufficiently large size to accommodate the signal label conjugate.

Of course, the signal repressor need not be porous, particularly where the particle conjugate is porous, since the bulk of the signal repressor particle will inhibit its entry into any pores or indentations of the particle conjugate. Similarly, if the signal repressor particle is porous, the particle conjugate need not be porous, having the specific binding pair member bound to the surface of the particle. Thus, while both particles may be porous, preferably only one need be porous.

In addition, neither particle need be porous, where the bulk characteristics of the particles provide for repulsion, particularly steric repulsion. Thus, the nature of the particles may be varied widely, so long as the final result is that the signal repressor discriminates between signal label bound to the particle conjugate and the dissociated signal label.

MATERIALS

The components employed in the assay will be the particle conjugate, the signal label conjugate, the signal repressor, reagents which are the remaining members of the signal producing system, the analyte, and as appropriate poly(ligand analog). Employed in the preparation of the reagents will be particles or beads, the specific binding pair members, and members of the signal producing system.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
phosphoproteins
mucoproteins
chromoproteins
lipoproteins
nucleoproteins
glycoproteins
proteoglycans
unclassified proteins, e.g., somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
  $\alpha_1$-glycoprotein
$\alpha_1$X-Glycoprotein
Thyroxin-binding globulin
Inter-$\alpha$-trypsin-inhibitor
Gc-globulin
  (Gc 1-1)
  (Gc 2-1)
  (Gc 2-2)
Haptoglobin
  (Hp 1-1)
  (Hp 2-1)
  Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
  (IgG) or $\gamma$G-globulin
Mol. formula:
  $\gamma_2K_2$ or $\gamma_2\lambda_2$
Immunoglobulin A (IgA)
  or $\gamma$A-globulin
Mol. formula:
  $(\alpha_2K_2)''$ or $(\alpha_2\lambda_2)''$
Immunoglobulin M
  (IgM) or $\gamma$M-globulin
Mol. formula:
  $(\mu_2K_2)^5$ or $(\mu_2\lambda_2)^5$
Immunoglobulin D(IgD)
  or $\gamma$D-Globulin ($\gamma$D)
Mol. formula:
  $(\delta_2K_2)$ or $\delta_2\lambda_2)$
Immunoglobulin E (IgE)
  or $\gamma$E-Globulin ($\gamma$E)
Mol. formula:
  $(\epsilon_2K_2)$ or $(\epsilon_2\lambda_2)$
Free K and $\lambda$ light chains
Complement factors:
C'1
  C'1q
  C'1r
  C'1s
C'2
C'3
  $\beta_1$A
  $\alpha_2$D
C'4
C'5
C'6
C'7
C'8
C'9

Important blood clotting factors include:

| BLOOD CLOTTING FACTORS | |
|---|---|
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

Peptide and Protein Hormones

Parathyroid hormone
  (parathromone)
Thyrocalcitonin
Insulin
Glucagon

Relaxin
Erythropoietin
Melanotropin
    (melanocyte-stimulating hormone; intermedin)
Somatotropin
    (growth hormone)
Corticotropin
    (adrenocorticotropic hormone)
Thyrotropin
Follicle-stimulating hormone
Luteinizing hormone
    (interstitial cell-stimulating hormone)
Luteomammotropic hormone
    (luteotropin, prolactin
Gonadotropin
    (chorionic gonadotropin)

Tissue Hormones

Secretin
Gastrin
Angiotensin I and II
Bradykinin
Human placental lactogen

Peptide Hormones from the Neurohypophysis

Oxytocin
Vasopressin
Releasing factors (RF)
    CRF, LRF, TRF, Somatotropin-RF, GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrheae | Polysaccharide |
| Corynebacterium diphtheriae | Polysaccharide |
| Actinobacillus mallei: | Crude extract |
| Actinobacillus whitemori | |
| Francisella tularensis | Lipopolysaccharide |
| | Polysaccharide |
| Pasteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and turberculin |
| Klebsiella aerogenes | Polysaccharide |
| Klebsiella cloacae | Polysaccharide |
| Salmonella typhosa | Lipopolysaccharide |
| | Polysaccharide |
| Salmonella typhi-murium: | Polysaccharide |
| Salmonella derby | |
| Salmonella pullorum | |
| Shigella dysenteriae | Polysaccharide |
| Shigella flexneri | |
| Shigella sonnei | Crude, Polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria

*Corynebacterium diptheriae*

Pneumococci

*Diplococcus pheumoniae*

Streptococci

*Streptococcus pyogenes*
*Streptococcus salivarus*

Staphylococci

*Staphylococcus aureus*
*Staphylococcus albus*

Neisseriae

*Neisseria meningitidis*
*Neisseria gonorrheae*

| Enterobacteriaciae | |
|---|---|
| *Escherichia coli* | } The coliform bacteria |
| *Aerobacter aerogenes* | |
| *Klebsiella pneumoniae* | |
| *Salmonella typhosa* | } The Salmonellae |
| *Salmonella choleraesuis* | |
| *Salmonella typhimurium* | |
| *Shigella dysenteriae* | } The Shigellae |
| *Shigella schmitzii* | |
| *Shigella arabinotarda* | |
| *Shigella flexneri* | |
| *Shigella boydii* | |
| *Shigella Sonnei* | |
| Other enteric bacilli | |
| *Proteus vulgaris* | } Proteus species |
| *Proteus mirabilis* | |
| *Proteus morgani* | |
| *Pseudomonas aeruginosa* | |
| *Alcaligenes faecalis* | |
| *Vibrio cholerae* | |
| Hemophilus-Bordetella group | |
| *Hemophilus influenzae.* | *H. ducreyi* |
| | *H. hemophilus* |
| | *H. aegypticus* |
| | *H. parainfluenzae* |
| *Bordetella pertussis* | |

Pasteurellae

*Pasteurella pestis*
*Pasteurella tulareusis*

Brucellae

*Brucella melitensis*
*Brucella abortus*
*Brucella suis*

Aerobic Spore-forming Bacilli

*Bacillus anthracis*
*Bacillus subtillis*
*Bacillus megaterium*
*Bacillus cereus*

Anaerobic Spore-forming Bacilli

*Clostridium botulinum*
*Clostridium tetani*
*Clostridium perfringens*
*Clostridium novyi*
*Clostridium septicum*
*Clostridium histolyticum*
*Clostridium tertium*
*Clostridium bifermentans*
*Clostridium sporogenes*

Mycobacteria

*Mycobacterium tuberculosis hominis*
*Mycobacterium bovis*
*Mycobacterium avium*
*Mycobacterium leprae*
*Mycobacterium paratuberculosis*

Actinomycetes (fungus-like bacteria)

*Actinomyces israelii*
*Actinomyces bovis*
*Actinomyces naeslundii*
*Nocardia asteroides*
*Nocardia brasiliensis*

---

The Spirochetes

| | |
|---|---|
| *Treponema pallidum* | Spirillum minus |
| *Treponema pertenue* | Streptobacillus moniliformis |
| *Treponema carateum* | |
| *Borrelia recurrentis* | |
| *Leptospira icterohemorrhagiae* | |
| *Leptospira canicola* | |

---

Mycoplasmas

*Mycoplasma pneumoniae*

Other pathogens

*Listeria monocytogenes*
*Erysipelothrix rhusiopathiae*
*Streptobacillus moniliformis*
*Donvania granulomatis*
*Bartonella bacilliformis*

Rickettsiae (bacteria-like parasites)

*Rickettsia prowazekii*
*Rickettsia mooseri*
*Rickettsia rickettsii*
*Rickettsia conori*
*Rickettsia australis*
*Rickettsia sibiricus*
*Rickettsia akari*
*Rickettsia tsutsugamushi*
*Rickettsia burnetii*
*Rickettsia quintana*

Chlamydia (unclassifiable parasites bacterial/viral)
Chlamydia agents (naming uncertain)

Fungi

*Cryptococcus neoformans*
*Blastomyces dermatidis*
*Histoplasma capsulatum*
*Coccidioides immitis*
*Paracoccidioides brasiliensis*
*Candida albicans*
*Aspergillus fumigatus*
*Mucor corymbifer* (*Absidia corymbifera*)

---

| | |
|---|---|
| *Rhizopus oryzae* | |
| *Rhizopus arrhizus* | Phycomycetes |
| *Rhizopus nigricans* | |

---

*Sporotrichum schenkii*
*Fonsecaea pedrosoi*
*Fonsecaea compacta*
*Fonsecaea dermatidis*
*Cladosporium carrionii*
*Phialophora verrucosa*
*Aspergillus nidulans*
*Madurella mycetomi*
*Madurella grisea*
*Allescheria boydii*
*Phialosphora jeanselmei*
*Microsporum gypseum*
*Trichophyton mentagrophytes*
*Keratinomyces ajelloi*
*Microsporum canis*
*Trichophyton rubrum*
*Microsporum andouini*

Viruses

Adenoviruses

Herpes Viruses

Herpes simplex
Varicella (Chicken pox)
Herpes Zoster (Shingles)
Virus B
Cytomegalovirus

Pox Viruses

Variola (smallpox)
Vaccinia
Poxvirus bovis
Paravaccinia
Molluscum contagiosum

Picornaviruses

Poliovirus
Coxsackievirus
Echoviruses
Rhinoviruses

Myxoviruses

Influenza (A, B, and C)
Parainfluenza (1-4)
Mumps Virus
Newcastle Disease Virus
Measles Virus
Rinderpest Virus
Canine Distemper Virus Respiratory Syncytial Virus
Rubella Virus

Arboviruses

Eastern Equine Eucephalitis Virus
Western Equine Eucephalitis Virus
Sindbis Virus
Chikugunya Virus
Semliki Forest Virus
Mayora Virus
St. Louis Encephalitis Virus
California Encephalitis Virus
Colorado Tick Fever Virus
Yellow Fever Virus
Dengue Virus

Reoviruses

Reovirus Types 1-3

Hepatitis

Hepatitis A Virus
Hepatitis B Virus

Tumor Viruses

Rauscher Leukemia Virus
Gross Virus
Maloney Leukemia Virus

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids, isoquinoline alkaloids; quinoline alkaloids; which includes quinine and quinidine; diterpene alkaloids, their derivatives and metabolites.

The next group of drugs includes steroids, which includes the estrogens, gestrogens, androgens, andrenocortical steroids, bile acids, cardiotonic glycosides and aglycones, which includes digoxin and digoxigenin, saponins and sapogenins, their derivatives and metabolites. Also included are the steriod mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites.

The next group of drugs is aminoalkylbenzenes, with alkyl of from 2 to 3 carbon atoms, which includes ephedrine, L-dopa, epinephrine, narceine, papverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met- and leu-enkephalin their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 6000,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

Ligand Analog

The ligand analog will differ from the ligand either by replacement of a hydrogen or a functionality with a bond or a linking group which has a functionality for forming a covalent bond to another molecule having an active functionality, such as an hydroxyl, amino, aryl, thio, olefin, etc., where the resulting compound differs from the ligand by more than substitution of a hydrogen by the molecule to which it is conjugated. The linking group will normally have from 1-20 atoms other than hydrogen, which are carbon, oxygen, sulfur, nitrogen, and halogen of atomic number 17-35. The functionalities which are involved include carbonyl, both oxo and nonoxo, active halogen, diazo, mercapto, ethylene, particularly activated ethylene, amino, and the like. The number of heteroatoms will generally range from about 0-6, more usually from about 1-6, and preferably from about 1-4. A description of linking groups may be found in U.S. Pat. No. 3,817,837, which disclosure is incorporated herein by reference.

For the most part, the linking groups will be aliphatic, although with diazo groups, aromatic groups are involved. Generally, the linking group is a divalent chain having about 1–10, more usually from about 1–6 atoms in the chain. Oxygen will normally be present as oxo or oxy, bonded to carbon and hydrogen, preferably bonded solely to carbon, while nitrogen will normally be present as amino, bonded solely to carbon, or amido, while sulfur would be analogous to oxygen.

Common functionalities in forming the covalent bond between the linking group and the molecule to be conjugated are alkylamine, amide, amidine, thioamide, urea, thiourea, guanidine, and diazo.

Linking groups which find particular application with conjugation to polypeptides are those involving carboxylic acids which may be used in conjunction with diimides, or mixed anhydrides with carbonate monesters or as active carboxlic esters e.g. N-hydroxy succinimide or p-nitrophenyl. Nitrogen analogs may be employed as imidoesters. Aldehydes can be used to form imines under reductive amination conditions e.g. in the presence of borohydrides, to produce alkylamines. Other non-oxo carbonyl groups which may be employed include isocyanates and isothiocyanates. In addition, active halide may be employed, particularly bromoacetyl groups.

In most instances, the ligand will have one or more functional groups which may be employed as the site for linking the linking group. Particularly, hydroxy, amino and aryl grpus, particularly activated aryl groups find use. Also, oximes may be prepared from oxo functionalities and the hydroxyl used as a site for joining to a linking group, such as carboxymethyl.

The choice of linking group will vary widely, depending upon the functionalities which are present in the ligand, in the compound to which the ligand is to be conjugated, the nature and length of the linking group desired, and the like.

Signal Producing System

The signal producing system includes the reagents and products involved in the production of a detectable signal. The signal producing system will have at least one reagent member, and may have two or more members. The level of the observed signal will be influenced by the partitioning of the signal label between the particle conjugate and the bulk solution. That is, whether the signal label is within the steric constrant of the particle or free in the bulk solution and accessible to the signal repressor. The particle conjugate must provide an environment which obstructs the signal repressor from diminishing the signal resulting from signal label bound to the particle conjugate. In addition, it is desirable that the signal producing system provide for several measurable events in response to the binding between the members of a single specific binding pair (amplification).

The signal producing system will involve the absorption or emission of light by a chromogen. The detectible signal may be a result of residual light after absorption by the chromogen of irradiated light (where the signal label is a dye), emitted light after absorption by the chromogen of irradiated light (where the signal label is a fluorescer or phosphor) or emitted light after a chemical reaction (where the signal label is a chemiluminescer). While the above situations will predominate, other reagents or combinations may also find use, such as energy transfer to an acceptor molecule.

The signal producing system may involve a chromogen as the signal label which absorbs or emits light on irradiation or the formation of such a chromogen. In the latter case, the signal label will be a compound which upon chemical reaction will undergo a substantial change in its spectroscopic properties, such as its light absorption properties, fluorescent properties or chemiluminescent properties. For the most part this change will be achieved by the cleavage of a labile bond or by a catalysed redox reaction, both reactions usually employing enzymes, to produce the desired chromogenic dye, fluorescer or chemiluminescer. Enzymes can also be advantageously employed with chemiluminescers.

The signal labels of primary interest are fluorescent signal labels and these will be considered first.

The fluorescers of interest will generally emit light at a wavelength about 350 nm, usually above 400 nm and preferably above 450 nm. Desirably, the fluorescers have a high quantum efficiency, a large Stokes shift and are chemically stable under the conditions of their conjugation and use.

Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates.

Individual fluorescent compounds which have functionalities for linking or can be modified to incorporate such functionalities include dansyl chloride, fluoresceins such as 3,6-dihydroxy-9-phenylxanthhydrol, rhodamineisothiocyanate, N-phenyl 1-amino-8-sulfonatonaphthalene, N-phenyl 2-amino-6-sulfonatonaphthalene, 4-acetamido-4'-isothiocyanatostilbene-2,2'-disulfonic acid, pyrene-3-sulfonic acid, 2-toluidinonaphthalene-6-sulfonate, N-phenyl, N-methyl 2-amino-naphthalene-6-sulfonate, ethidium bromide, atebrine, auromine-0,2-(9'-anthroyl)palmitate, dansyl phosphatidylethanolamine, N-(p-2-benzimidazolyl)phenyl)maleimide, 4-phenylspiro(furan-2.1'-phthalan)-3,3'-dione, homovanilic acid dimer, N,N-dioctadecyl oxacarbocyanine, N,N'-dihexyl oxacarbocyanine, merocyanine, 4-(3'-pyrenyl)butyrate, d-3-aminodesoxyequilenin, 12-(9'-anthroyl)stearate, 2-methylanthracene, 9-vinylanthracene, 2,2'-vinylene-p-phenylene)bis-benzoxazole, p-bis[2-(4-methyl-5-phenyloxazolyl)]benzene, 6-dimethylamino-1,2-benzophenazin, retinol, bis(3'-aminopyridinium) 1,10-decandiyl diiodide, sulfonapthyl hydrazone of hellebrigenin, chlortetracycline, N-(7-dimethylamino-4-methyl-2-oxo-3-chromenyl) maleimide, N-[p-(2-benzimidazoyl)-phenyl] maleimide, N-(4-fluoranthyl) maleimide, bis(homovanillic acid), resazarin, 4-chloro-7-nitro-2.1.3-benzooxadiazole, merocyanine 540, resorufin, rose bengal, 2,4-diphenyl-3(2H)-furanone, methylumbelliferone, 9,10-dibromoanthracene, 9,10-diethinylanthracene, and eosin.

It should be noted that the absorption and emission characteristics of the bound chromogen may differ from the unbound chromogen. Therefore, when referring to the various wavelength ranges and characteristics of the chromogen, it is intended to indicate the chromogens as employed and not the chromogen which is unconjugated and characterized in an arbitrary solvent.

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

A diverse number of families of compounds have been found to provide chemiluminescence under a variety of conditions. One family of compounds is 2,3-dihydro-1,-4-phthalazinedione. The most popular compound is luminol, which is the 5-amino compound. Other members of the family include the 5-amino-6,7,8-trimethoxy-and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents.

Various dyes may be employed which absorb light above 300 nm, preferably above 350 nm and more preferably above 400 nm. In choosing a dye, the dye should be subject to a substantial change in its spectrum when bound to the signal repressor.

Illustrative dyes include phenolics, azo compounds, triarylmethanes, phthaleins and the like. The dyes can be modified to introduce a functionality for covalent bonding to the member of the specific binding pair, whenever such group is not present as commercially available.

Illustrative dyes include medola blue, methylene blue, alizarin, nitrophenols, fuchsin, aniline yellow, para red, indigo, phthalocyanine, and naphthol-AS.

Besides the chromogens, chromogen precursors can be employed which by undergoing a chemical reaction produce the desired chromogen. Conveniently, the reaction may involve a catalyst, both enzymatic and non-enzymatic, and chemical transformations, such as hydrolysis and reduction-oxidation reactions.

In the hydrolytic reactions, normally a phenolic chromogen will be coupled to a group by a enzyme labile bond, where the substituted phenol has substantially different chromogenic properties from the unsubstituted phenol e.g. non-fluorescent to fluorescent. Examples would be glycosidyl fluoresceins cleaved by glycosidasis e.g. $\beta$-galactosidase and umbelliferyl phosphate cleaved by acid or alkaline phosphatase.

Alternatively, one could employ the leuco form of a chromogen and catalytically, either enzymatic or non-enzymatic, or non-catalytically, oxidize or reduce the chromogen to the active or colored form. For example, fluorescin may be oxidized to fluorescein, phenazine methosulfate may be reduced by NADH produced by an NAD dependent dehydrogenase, methylene blue may be oxidized with a hemoflavoprotein, and benzyl viologen may be oxidized with xanthine oxidase. Non-enzymatic reductants or oxidants may also be used.

The enzymes of interest will for the most part be in I.U.B. Class I, oxidoreductases or I.U.B. Class III, hydrolases.

By employing chromogen precursors, one can employ a rate mode rather than an equilibrium mode for determination of the signal. By allowing the signal label conjugate to bind to the particle conjugate, the observed signal will be primarily from the signal label associated with the particle conjugate, since the signal repressor will repress the production of signal produced by chromogen in the bulk solution.

Particles

A wide variety of solid or liquid, usually solid, particles may be employed in this invention. For many of the methods, at least one of the particles is porous or microreticulated, that is, has areas open to the bulk solution, which are greater than about 50% encompassed by the particle material. These areas can be deep pores, channels, fractures, indentations or the like.

The particles which are employed are chosen to obstruct the interaction between signal label bound to the particle conjugate and the supressor sites or functionalities of the signal repressor. By appropriate employment of insoluble particles, one can limit the accessibility of a signal label on the particle surface to the signal repressor. With porous particles, the pores or channels of the particle are chosen to permit access of at least one member of the signal producing system and to inhibit access of the signal repressor.

The porous solid particles can come with various pore sizes. The pore size will be chosen in accordance with the property of the particle which is being employed. Where the diffusion rate is a significant factor, one will employ a cut-off size between the molecules which must diffuse into the pores and the molecules which are inhibited from diffusing into the pores. Cut-off sizes can vary from tens of thousands e.g. 20,000, more usually 40,000 to millions molecular weight e.g. 10,000,000, more usually 1,000,000 and various ranges are commercially available.

The size of the solid particle is limited by the following considerations. The particles should be relatively stably dispersed during the time of the assay and preferably longer. Indefinite stability in the assay medium is not required. The particle size should be sufficiently small, so that a large number of particles will be in the solution. That is, one does not wish to see wide fluctuations in the signal, where one or a few particles passing through the light path make a substantial change in the observed signal. Therefore, for the most part, the particles will be of a diameter in the range of about 50 nm to 100$\mu$, more usually about 500 nm to 5$\mu$. Pores sizes will generally vary from about 0.1 nm to under 750 nm, more usually not more than about 500 nm.

The particle size can be varied and surface area increased by breaking larger particles into smaller particles by mechanical means, such as grinding, sonication, agitation, etc.

A wide variety of materials may be employed for the particles. Many materials are commercially available or commerically available materials may be modified, so as to modify the properties of the material.

The particles can be derived from naturally occurring materials, naturally occurring materials which are synthetically modified and synthetic materials. Of particular interest are polysaccharides, particularly cross-linked polysaccharides, such as agarose, which is available as Sepharose, dextran, available as Sephadex and Sephacyl, cellulose, starch and the like. Other materials include polyacrylamides, polystryene, polyvinyl alcohol, copolymers of hydroxyethylmethacrylate and methyl methacrylate, silicones, glasses, available as Bioglas, charcoal and the like.

The particles will usually be polyfunctional or be capable of being polyfunctionalized. A wide variety of functional groups are available or can be incorporated. Functional groups include carboxylic acids, aldehydes, amino groups, cyano groups, ethylenic groups, hydroxyl groups, mercapto groups, and the like. The manner of linking a wide variety of compounds to the various particles is well known and is amply illustrated in the literature. See for example, Cuatrecases, J. Biol. Chem. 245, 3059 (1970).

The length of the linking groups will vary widely depending upon the nature of the compound being linked, the effect of distance between the label and the particle on the labels properties, the potential for crosslinking of the label, and the like.

Discrete liquid particles may be employed as the signal repressor. These particles can be oil droplets stably dispersed by means of a surfactant, liposomes or the like, where light absorption capability is imparted to the particle. For oil droplets, a black lipophilic dye could be introduced into the oil. For liposomes, quenching molecules can be bonded to the membrane lipids. In each instance, antichromogen would also be bonded to the particle surface.

Particle Conjugate

The particle conjugate will always be conjugated to one of the members of the specific binding pair. The conjugation may be direct or indirect. By direct conjugation is intended covalent bonding of the specific bonding pair member label to the particle. Alternatively, one can employ receptor for the specific binding pair member. Where the specific binding pair member is multivalent, an impure preparation of a complementary member may be covalently bonded to the particle. Non-covalent binding of the unpurified specific pair member then gives a particle labelled with the homologous pair member free of contaminants. The resulting particle conjugate may then be used in the assay with its complementary signal label conjugate.

A modification of the above situation may be employed where the analyte is a receptor such as human IgE. One could covalently bond an allergen recognized by the IgE to the particle. As the signal label conjugate one could use sheep anti(human IgE). In the assay, the human IgE analyte would bind to the allergen on the particle and the signal label conjugate (anti(human IgE)) would bind to the human IgE bound to the particle. This situation differs from the general situation since the binding of the analyte to the particle during the assay produces what has been defined as the particle conjugate. Also, other receptors such IgA, IgG, IgM, enzymes, specific receptors such as for estriol, biotin or other drugs, etc. may be similarly employed.

In effect, there are two specific binding pairs, where the same compound plays the role of antigen in one pair and receptor in the other, while the complementary members to the analyte of each of the specific binding pairs need not have any relationship of ligand and receptor.

The ratio of the specific binding pair member to the molecular weight of the particle will vary widely, depending upon the nature of the particle, the available surface area, the available binding sites, and the like. There will be on the average at least about one specific binding pair member per particle and generally at least about one per $1 \times 10^5$ molecular weight, more usually at least about one per $1 \times 10^7$ molecular weight.

Signal label conjugate

The conjugation of labels to ligands and receptors, has been amply reported in the literature, particularly in the references cited previously. Mole ratios of labels to specific binding pair member will vary widely, depending upon the nature of the label as well as the nature of the specific binding pair member.

The number of labels conjugated to the member of the specific binding pair will be on the average at least one and not more than the molecular weight of the member divided by 1,500, usually not more than the molecular weight divided by 3,000, generally in the range of about 1 to 50, usually in the range of about 2 to 30.

In some instances it may be feasible to have one or more molecules of a member of the specific binding pair conjugated to a label; usually less than one molecule per 1,500 molecular weight. The number of molecules per label will generally be less than 50, usually less than 30, and more usually less than 10.

The method of linking will conveniently involve stable covalent bonds, where the signal label may be joined to the member by a bond or a spacer arm of from about 1 to 10 atoms chain length.

Signal Repressor

The signal repressor can be varied widely so long as the particle is capable of preferentially affecting the emission of light from the assay medium by differentiating between the signal label in the bulk solution as compared to signal label bound to the particle conjugate. The particle employed for the signal repressor will have one or more of the following properties: absorption in the wavelength range of light emitted by the signal producing system as the detectible signal; ability to accept or degrade energy from an excited molecule, so as to inhibit the emission of light; inhibition of the excitation of the emitting molecule by absorption of light at the excitation wave lengths.

The size of the signal repressor particle may vary widely, generally being in the range of about 50 nm to 100$\mu$, usually 500 nm to 5$\mu$. The limitation on the size of the particle is that it should not unduly obstruct the entering or exiting of light from the assay medium, which is unrelated to the signal label in proximity to the signal repressor, nor should it create substantial fluctuations in signal due to its movement through the measurement zone of a device for measuring electromagnetic radiation.

Various particles may be employed which may be conjugated, covalently or non-covalently, with receptor for the signal label conjugate—usually receptor for the signal label—or receptors for the binding pair member of the signal label conjugate as well as for impurities associated with the binding pair member.

Alternatively, signal repressor particles may have an inherent affinity for the signal label due to naturally present active center sites which bond to particular conformations e.g. extended aromatic conjugated systems, particularly chromophoric. In addition, active center sites could be synthetically introduced by chemical modification e.g. sulfhydryl groups could be attached to the signal label and a sulfhydryl specific reagent bonded to the signal repressor particle. Many other combinations of coupling groups could be employed.

The particles which are employed can be adsorptive or non-adsorptive to proteins; the particles may be naturally occurring, synthetic or combinations thereof, a single material or mixture of materials, and are normally chemically inert, absorb light in the wavelength range of interest and are frequently black. Illustrative materials include particles of carbon, such as activated charcoal, lamp black, graphite and colloidal carbon, colloidal metal particles, metal oxide particles, metal chalcogenide particles, light absorbing synthetic polymeric particles, etc.

The particles must be dispersable in the assay medium and should provide a relatively stable dispersion or be capable of a relatively stable dispersion by virtue of the addition of a dispersant. It is only necessary that the particles remain dispersed during the period of measurement, although longer times are desirable.

While the manner in which each type of particle represses light emission will vary, one or more of the following factors may be involved wholly or in part: energy acceptance; shielding; light absorption or perturbation of energy levels through chemical or physical interaction with the particle surface.

The solid particles of the signal repressor may be individual particles or associations or aggregations of particles, either with each other or with different particles or macromolecular substances, which may or may not be light absorbing. Illustrative types of materials include polysaccharides e.g. agarose, cellulose, Sephadex, and dextran, silica, and the like. These aggregations can be employed to enhance the capacitiy of the signal repressor particles for the absorption of the signal label and/or to reduce the rate of settling, by varying the density and shape of the signal repressor particle aggregation.

Ancillary Materials

Various ancillary materials may be employed in the subject assays. Normally, sufficient buffering agent will be employed to provide a buffer concentration from about 0.01 to 1 M. In addition to buffers, other materials may be added: stabilizers such as proteins e.g. albumins, in amounts to provide a concentration up to about 1.5 weight percent; protective compounds, such as bacteriostats or bacteriocides e.g. sodium azide, in amounts to provide concentrations up to about 1 weight percent; as well as other materials for specific effects, such as surfactants, chelating agents, or oxidation inhibitors.

In addition, other reagents will be employed in conjunction with the requirements of the signal producing systems. Such reagents may include energy donors or acceptors, enzymes, acidic or basic reagents, or the like.

Kits

As a matter of convenience, the reagents can be provided as kits, where the reagents are in predetermined ratios, so as to substantially optimize the sensitivity of the assay in the range of interest. When lyophilized, after reconstitution of the reagents, the particle conjugate as well as the signal repressor will normally be dispersed in an aqueous medium of substantially the same density as the particle, so that the particles remain substantially uniformily dispersed or dispersible. By employing high density additives or adjusting the density of the particles, the desired density relationship can be achieved.

The signal repressor particle will normally be added in at least about sufficient amount to bind substantially ($\geqq 90\%$) all of the signal label. The amount of the particle conjugate will be sufficient to provide a dynamic assay range in accordance with the range of interest of the analyte. The amount of signal label conjugate will be matched with the amount of particle conjugate.

The reagents provided in the kits will be the particle conjugate, the signal label conjugate and the signal repressor. Depending upon the particular materials and protocol, the signal label conjugate and particle conjugate may be combined as a single reagent in conjunction with various other reagents, such as stabilizers, proteins, buffers, and the like. The amount of each individual stabilizer will be sufficient to provide a concentration in the reagent solution prepared for employing in the assay in the range of about 0.01 to 1 weight percent. The amount of buffer will be sufficient to provide concentrations in the reagent solution in the range of about 1 mM to 1 M. The signal repressor can be employed in relatively large excess over the amount necessary to bind about 90% of the signal label, to insure that all of the signal label in the bulk solution is rapidly inhibited from producing a signal.

For convenience in performing the immunoassay, it is desireable to be able to combine a plurality of reagents in a single container, so that the reagents may be added simultaneously in carefully related ratios. Where the signal label conjugate or the signal repressor can be combined in a form where the signal label weakly binds, if at all, to the signal repressor, the two reagents may be combined in a single vial.

For example, by employing a chromogen as the signal label in its leuco form, such as a chromogen precursor, as its protonated form rather than as its salt, or as the reduced or oxidized form, where such state is colorless, the chromogen will bind weakly to a signal repressor such as charcoal. Where the signal repressor has antichromogen, the leuco form in many instances may bind weakly, if at all, to the antichromogen.

When combining the signal label conjugate with the signal repressor in a single vial, one can also include appropriate buffers, so that an aqueous solution would be at an appropriate pH to minimize binding of signal label to the signal repressor.

Where the signal label and signal repressor are combined as a single reagent for performing the assay, one would normally add the analyte containing sample to the combined reagent prior to adding the particle conjugate and any additional reagents for transforming the signal label to the chromogenic form. If desired, one could combine such reagents with the particle conjugate, so that only two reagents would be required in the laboratory.

EXPERIMENTAL

The following examples are offered by way of illustration and not by way of limitation.

(All temperatures not otherwise indicated are in centigrade. All parts or percents not otherwise indicated are by weight, except for mixtures of liquids which are by volume. The following abbreviations employed: RT-room temperature; anti HuIgG-antibodies to human IgG; DMF-N,N-dimethyl formamide; PBS-phosphate buffered saline.)

EXAMPLE 1

Coupling of Anti-Fluorescein to Charcoal

Into 2 ml water was dispersed 50 mg activated charcoal and the mixture sonicated with a Branson Cell Disruptor, Model 35, cup horn, 50% pulse, setting 5, for 2 minutes. A total of 10 mg of an antifluorescein composition was diluted to 3 ml with PBS pH7.8 (0.05% NaN$_3$) followed by the addition of 40 μl of $^{14}$C sheep IgG and 70 μl buffer and 110 μl taken for radioactive counting (10 ml aquasol, 5746 cpm/100 μl). The 3 ml of the antifluorescein was combined with the sonciated charcoal dispersion and the mixture stirred overnight at r.t.

The mixture was then centrifuged, 0.5 ml was taken from the supernatant, the pellet washed 5× with PBS pH7.8, (0.05% NaN$_3$) a sixth time with 5 ml, which wash was then repeated with 1 ml aliquots taken to determine whether protein was still present in the washes. The pellet was then resuspended in PBS (2 ml). Based on the radioactivity of the charcoal dispersion and correcting for the reduction in cpm resulting from the presence of charcoal, approximately 3.9 mg of antifluorescein is bound to 50 mg charcoal.

EXAMPLE 2

Fluorescein Labeling of AntiHuIgG

A. To 0.5 ml of antiHuIgG (5 mg Dako 10-mat 046) which had been dialyzed against 0.1 M sodium carbonate, pH9.0, was added 0.2 mg of fluoresceinisothiocyanate in 50 ml of DMF and the mixture stirred at RT for 3 hrs. The mixture was then chromatographed on a Sephadex G-25 column in PBS, pH7.0. The product was isolated in a solution having 3.2 mg/ml and the fluorescein/protein ratio was found to be 11.2. Approximately 25% of the fluorescein was found to be bound to antiHuIgG by precipitation with HuIgG bound to Sepharose-4B.

B. The above reaction was repeated as follows.

To 0.5 ml antiHuIgG (Dako, 10-mat, Lot 046, approximately 10 mg/ml) dialyzed against 0.1 M sodium carbonate, pH9.0) was added 10 μl of 0.1 mg fluoresceinisothiocyanate in 100 μl DMF and the mixture stirred at RT for 1 hr in the dark. The reaction mixture was then chromatographed on a Sephadex G-25 column in PBS, pH7.0. The product had a concentration of 4.95 mg/ml with a fluorescein/protein ratio of 0.47.

EXAMPLE 3

Coupling of HuIgG to Sepharose-CL6B)

To approximately 2 ml of SepharoseCL 6B beads (Pharmacia) previously washed with 1 M sodium carbonate was added 150 l of a solution of CNBr in acetonitrile at a concentration of 2 g/ml and the mixture stirred for 2.5 min. The beads were isolated and then washed with 0.1 M sodium carbonate, pH9.1, water and 0.1 M sodium carbonate, pH9.1. To the beads were then added 2.9 ml of a HuIgG solution (5.6 mg/ml) and the resulting mixture agitated overnight at 4°. To the mixture was then added 0.5 ml of 1 M aminopropanol, pH8.0, and the mixture agitated for 1 hr at 4°. The resulting beads were then washed three times each with a first aqueous solution 0.1 M sodium acetate, 1 M NaCl, pH4.0; and a second solution 0.1 M sodium borate, 1.0 M NaCl, pH8.0. The beads were then sonicated for 0.5 hr with a Branson Cell Disrupter, No. 2 setting, microtip. By employing a radioactive label, it was found that 5.6 mg HuIgG was present for 1 ml of beads.

In a first assay to demonstrate the subject invention, an adsorptive material, charcoal was employed, for quenching the fluorescin. Adsorptive MCB activated Norit A CX655 charcoal was mixed with water at a concentration of 1.5 mg/ml and the particles dispersed by a 2 min sonication with a Branson Cell Disruptor, Model 35, No. 2 setting. The fluorescein-anti-HuIgG employed was that of Example 2A having a fluorescein/protein ratio of about 14. The buffer employed was PBS, 0.5% sodium azide, 10 mM sodium phosphate, 0.15 M NaCl, pH7.8.

The fluorescein-antiHuIgG was at a concentration of about 3.2 mg/ml. The HuIgG-Sepharose CL6B which had a concentration of 5.6 mg of HuIgG/ml packed beads was sonicated with the Branson Cell Disruptor described above three times for 15 min periods, after each sonication spinning down the beads and washing them with buffer. The light absorption by the charcoal was determined at 520 nm as a correction factor. In a first series of tests, 15 μl of fluorescein-antiHuIgG (diluted 1:80; 5×10$^{-9}$ M) was combined with various volumes of charcoal solution and buffer added to provide a final volume of 0.75 ml. Setting the fluorescence in the absence of charcoal as 100%, 10 μl of the charcoal solution resulted in 17.5% of the original fluorescence, 25 μl in 1.4% of the original fluorescence and 50 μl in 0.06% of the original fluorescence. This demonstrated the quenching effect of the charcoal on fluorescein bonded to antibody.

In the next series of tests, 15 μl of fluorescein-antiHuIgG (diluted 1:20), 15 μl of HuIgG-Sepharose CL6B (diluted 1:3) and 100 μl of buffer were combined, incubated for 1 hr at RT, the mixture spun down and the pellet resulting from the beads washed with buffer. Approximately 50 μl of the bead pellet (5×10$^{-9}$ M in fluorescein-antiHuIgG and 2.1×10$^{-7}$ M in f HuIgG-Sepharose (CL6B) was combined with 650 μl of buffer and 50 μl of charcoal or 50 μl of buffer, and the mixture incubated for 0.5 hr at RT. Setting the fluorescence obtained with a combination of fluorescein-anti-HuIgG and HuIgG-Sepharose CL6B at 100% and correcting for light absorption by charcoal, the presence of charcoal resulted in 45.5% of the original fluorescence. Thus, the binding of the fluorescein to the Sepharose-CL6B through the intermediacy of the HuIgG and anti-HuIgG resulted in about 50% protection.

In the next assay, the effect of the presence of human IgG is shown. The protocol employed is similar to that previously described. The assay medium is prepared by combining 20 μl of fluorescein-antiHuIgG diluted 1/329 with 0.80 ml buffer (5×10$^{-9}$ M antibody), and 10 μl at varying dilutions incubating for 0.5 hr, adding 10 μl (4×10$^{-8}$ M) HuIgG-Sepharose CL6B (final concentration of 3.8×10$^{-7}$ M) or buffer, incubating for 0.5 hr, adding 20 μl of charcoal coated with antifluorescein and incubating for a final 0.5 hr. Readings are then taken as previously described. The following table indicates the results.

| HuIgG conc. Log$_{10}$ | % Fluorescence[a] |
| --- | --- |
| [b] | 7.6, 7.1 |
| −10 | 4.9, 4.4 |
| −9 | 2.1, 2.2 |
| −8 | 2.0, 1.5 |

[a]The % fluorescence is based on a value of 100% for fluorescein - HuIgG in buffer at the same concentration as in the assay medium.
[b]No HuIgG added, only an equivalent volume of buffer.

The above results demonstrate that assays can be developed which rely on protection of a label bound to a particle through the intermediacy of a specific binding pair from a particulate signal repressor which interacts with the label to repress the signal. The subject method provides many advantages. First, one can use relatively impure mixtures containing the desired member of the specific binding pair to prepare the particle conjugate, since any impurities will not interfere with the preparation or function of the particle conjugate.

Secondly, one can label relatively impure mixtures of the member of the specific binding pair with signal label, since the signal derived from the signal label bound to other than members of the specific binding pair will be substantially repressed. Finally, greatly enhanced sensitivity is achieved in that the signal from the signal label conjugate which is not bound to the particle conjugate is also repressed. Thus, background values which would add to the uncertainty of the assayed value are substantially diminished, both as to adventitious label, as well as the signal label conjugate which remains in the bulk solution.

The subject invention therefore provides sensitive and accurate assays for a wide variety of organic compounds or compositions, as well as reagents which may be prepared relatively easily, are stable for long periods of time, and when combined in an assay medium provide for results in relatively short times.

Although the foregoing invention has been described in some detail by way of illustration and example for purposes of clarity of understanding, it will be obvious that certain changes and modifications may be practiced within the scope of the appended claims.

What is claimed is:

1. A method for determining the presence in a sample of an analyte which is a member of a specific binding pair consisting of ligand and homologous antiligand, employing as reagents: (a) a member of said specific binding pair bound to a discrete dispersible particle to provide a particle conjugate; (b) a member of said specific binding pair conjugated to a member of a signal producing system to provide a signal label conjugate, wherein said signal producing system is capable of emitting ligh upon excitation of a member of said system, and (c) an opaque solid light absorptive signal repressor particle capable of modulating the signal producing capability of said signal label conjugate when bound to said signal label repressor, but inhibited from said modulating, when said signal label conjugate is bound to said particle conjugate;

said method comprising:
(1) combining in an aqueous assay medium, said sample, particle conjugate, signal label conjugate, and signal repressor,
with the proviso that when said member of the specific binding pair is the same for said analyte, particle conjugate and signal label conjugate, the homologous member is added; and
(2) determining at at least one wavelength the light emitted by said signal producing system in said aqueous assay medium.

2. A method according to claim 1, wherein said aqueous assay medium is at a temperature in the range of about 10° to 50° C. and at a pH in the range of about 5 to 10.

3. A method according to claim 2, wherein said signal producing system includes a fluorescer emitting light at a wavelength greater than 400 nm.

4. A method according to claim 2, wherein said signal producing system includes a chemiluminescent molecule.

5. A method according to any of claims 2 to 4 wherein said signal repressor particle comprises carbon.

6. A method according to claim 5, wherein said carbon signal repressor particle is charcoal.

7. A method according to any of claims 2 to 4 wherein receptor for said signal label is bound to said signal repressor particle.

8. A method according to claim 1, wherein said signal label reacts with an enzyme prior to production of said signal and said enzyme is a member of said signal producing system.

9. A method according to claim 8, wherein said signal label is a fluorescer precursor.

10. A kit for use in a method according to claim 1, for determining a member of a specific binding pair consisting of ligand and antiligand, said kit comprising a particle conjugate consisting essentially of a member of said specific binding pair bound to a discrete dispersible solid particle; a signal label conjugate consisting essentially of a member of a signal producing system capable of emitting light upon excitation of one of its members conjugated to a member of said specific binding pair; and an opaque solid particle capable of repressing the emission of light of said signal label conjugate when said signal label conjugate is bound to said particle, wherein when said signal label conjugate is bound to said particle conjugate through the intermediacy of said specific binding pair, said opaque particle is inhibited from binding to said signal label conjugate and repressing the emission of light of said signal label conjugate.

11. A kit according to claim 10, wherein said signal repressor particle is charcoal.

12. A method for determining the presence in a sample of a ligand analyte, wherein the ligand with its homologous antiligand define a specific binding pair,
wherein said method employs as reagents (a) a member of said specific binding pair bound to discrete dispersible solid particles to provide a particle conjugate; (b) a member of said specific binding pair conjugated to a member of a signal producing system to provide a signal label conjugate, wherein said signal producing system is capable of emitting light upon excitation of a member of said system; and (3) an opaque solid signal repressor particle capable of repressing light emission when said signal label conjugate is bound to said signal repressor, but inhibited from repressing light emission when said signal label conjugate is bound to said particle conjugate;
said method comprising:
(1) combining in an aqueous medium at a pH in the range of about 6.5 to 9.5 said sample, particle conjugate, signal label conjugate, and signal repressor,
with the proviso that when said member of said specific binding pair is the same for said analyte, particle conjugate and signal label conjugate, the homologous member is added; and
(2) determining at at least one wavelength, the light emitted by said signal producing system in said aqueous assay medium.

13. A method according to claim 12, wherein said ligand is a poly(amino acid).

14. A method according to claims 12 or 11, wherein said signal producing system includes a fluorescer bound to antiligand which emits light at a wavelength greater than 400 nm.

15. A method according to claim 14, wherein said fluorescer is a fluorescein.

16. A method according to any of claims 12 or 13, wherein said signal repressor particle comprises carbon.

17. A method according to claim 16, wherein said carbon signal repressor particle is charcoal.

18. A method according to claim 16, wherein receptor for signal label is bound to said signal repressor particle.

19. A method according to claim 16, wherein receptor for impurities in said sample is bound to said signal repressor particle.

20. A method for determining the presence in a sample of a receptor analyte, which is a member of two specific binding pairs, a first pair, where said receptor is antiligand to its homologous ligand and a second pair where said receptor is the ligand to its homologous antireceptor, so that in the assay method, ligand, receptor analyte and antireceptor are present, employing as reagents (a) ligand bound to discrete dispersible solid particles to provide a particle conjugate; (b) antireceptor conjugated to a member of a signal producing system to provide a signal label conjugate, wherein said signal producing system is capable of emitting light upon excitation of a member of said system; and (c) an opaque solid signal repressor particle capable of repressing light emission when said signal label conjugate is bound to said signal repressor, but inhibited from repressing said signal label when bound to said particle conjugate;

said method comprising (1) combining in an aqueous assay medium at a pH in the range of about 5 to 10 and at a temperature in the range of about 10° to 50° C. said sample, particle conjugate, signal label conjugate, and signal repressor; and (2) determining at at least one wavelength the light emitted by said signal producing system in said aqueous assay system.

21. A method for determining the presence in a sample of (a) globulin analyte, said globulin being a member of a specific binding pair consisting of globulin and antiglobulin, employing as reagents globulin bound to discrete dispersible solid particles to provide a particle conjugate; (b) antiglobulin conjugated to a fluorescing molecule which emits light at wavelengths greater than about 450 nm to provide a signal label conjugate; and (c) charcoal particles as signal repressor particles;

said method comprising:

(1) combining in an aqueous assay medium, said sample, particle conjugate, signal label conjugate, and charcoal particles; and (2) determining at at least one wavelength the light emitted by said fluorescer upon irradiation with light absorbed by said fluorescer in said aqueous assay medium.

22. A method according to claim 21, wherein said globulin is an immunoglobulin, and said fluorescer is a fluorescein.

23. A method for determining the presence in a sample of an analyte which is a member of a specific binding pair consisting of ligand and homologous antiligand, employing as reagents: (a) a member of said specific binding pair bound to a discrete dispersible solid particle to provide a particle conjugate; (b) a member of said specific binding pair conjugated to a member of a signal producing system to provide a signal label conjugate, wherein said signal producing system is capable of modulating the amount of light exiting from said medium; and (c) an opaque solid signal repressor particle capable of affecting said light modulation when said signal label conjugate is bound to said signal label repressor, but inhibited from affecting said light modulation, when said signal label conjugate is bound to said particle conjugate;

said method comprising:

(1) combining in an aqueous assay medium, sample, particle conjugate, signal label conjugate, and signal repressor, with the proviso that when said member of the specific binding pair is the same for said analyte, particle conjugate and signal label conjugate, the homologous member is added; and (2) determining at at least one wavelength the light exiting from said assay medium.

* * * * *